(12) United States Patent
Stotzka et al.

(10) Patent No.: US 6,786,868 B2
(45) Date of Patent: Sep. 7, 2004

(54) ULTRASONIC TOMOGRAPH

(75) Inventors: Rainer Stotzka, Karlsruhe (DE); Werner A. Kaiser, Jena (DE); Hartmut Gemmeke, Stutensee (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 0 days.

(21) Appl. No.: 10/393,826

(22) Filed: Mar. 21, 2003

(65) Prior Publication Data

US 2003/0158481 A1 Aug. 21, 2003

Related U.S. Application Data

(63) Continuation-in-part of application No. PCT/EP01/11735, filed on Oct. 10, 2001.

(30) Foreign Application Priority Data

Oct. 11, 2000 (DE) .......................... 100 50 232

(51) Int. Cl.⁷ ................................. A61B 8/00
(52) U.S. Cl. ...................................... 600/437
(58) Field of Search ............... 600/437–472; 73/625, 626; 128/898, 916

(56) References Cited

U.S. PATENT DOCUMENTS

| | | | |
|---|---|---|---|
| 3,556,081 A | * 1/1971 | Jones ........................ 600/437 |
| 3,765,403 A | * 10/1973 | Brenden ..................... 600/448 |
| 4,075,883 A | 2/1978 | Glover | |
| 4,130,112 A | * 12/1978 | Frazer ........................ 600/448 |
| 4,282,880 A | * 8/1981 | Gardineer et al. .......... 600/437 |
| 4,298,009 A | * 11/1981 | Mezrich et al. ............. 600/443 |
| 4,338,948 A | * 7/1982 | Perez-Mendez et al. .... 600/437 |
| 4,341,222 A | * 7/1982 | Gardineer et al. .......... 600/437 |
| 4,347,850 A | * 9/1982 | Kelly-Fry et al. .......... 600/437 |
| 5,474,072 A | * 12/1995 | Shmulewitz ................ 600/446 |
| 5,673,697 A | 10/1997 | Bryan et al. | |
| 6,409,668 B1 | * 6/2002 | Wollschlaeger ............. 600/443 |
| 6,475,150 B2 | * 11/2002 | Haddad ...................... 600/448 |
| 2004/0064046 A1 | * 4/2004 | Shehada ..................... 600/437 |

FOREIGN PATENT DOCUMENTS

DE 28 27 423 1/1980
EP 0 782 099 12/1995

* cited by examiner

Primary Examiner—Ali Imam
(74) Attorney, Agent, or Firm—Klaus J. Bach

(57) ABSTRACT

In a high resolution ultrasonic tomograph operating according to transmission, scattering and impulse-echo methods, comprising a container with an open top and including ultrasonic transducers arranged along the walls of the container, a coupling medium disposed in the container and a computer-based control and evaluation unit with a working memory, the control and evaluation unit is connected in a circuit with the ultrasonic transducers in such a way that the ultrasonic signal emitted from at least one ultrasonic transducer forms an ultrasonic impulse which is received by all the other transducers in parallel and is amplified, filtered and digitized to form electric signals which are stored in the working memory as a data set.

4 Claims, 3 Drawing Sheets

ULTRASONIC TOMOGRAPH

This is a Continuation-In-Part application of international application PCT/EP01/11735 filed Oct. 10, 2001 and claiming the priority of German application 100 50 232.6 filed Oct. 11, 2000.

BACKGROUND OF THE INVENTION

The invention relates to an ultrasonic tomograph operating according to transmission, scattering and impulse echo methods for the examination of tissue of extremities particular the female breast tissue and the male reproduction organs.

In medical engineering, ultrasound examinations become increasingly important. At one hand, in contrast to X-radiation ultrasound does not damage the tissue being examined. On the other hand, tissue types can be distinguished by ultrasound imaging which, with other imaging procedures such as x-ray examination, provide for only very little contrast.

A medical ultrasonic apparatus consists essentially of an ultrasound head with a number of ultrasound transducers as well as a control unit and an evaluation unit which emits the control impulses for the ultrasound transducers and which receives the measuring signals obtained from the transducers as electrical signals. The electrical signals are amplified by the control unit and, during the measuring procedure, reconstructed on a screen for real-time imaging. The complexity of such a reconstruction in real time limits not only the number of individual transducers employed with such ultrasonic apparatus but also to a great extent the correction capabilities during the reconstruction. Furthermore, the ultrasonic heads are generally not stationary but are manually moved. These facts substantially limit the capabilities during examinations with contrast media in ultrasound mammography where high spatial and time resolution is very important for the reconstruction. An additional limitation is an insufficient reproducibility.

U.S. Pat. No. 4,478,083 discloses a system for ultrasound mammography using the impulse-echo procedure wherein the female breast is inserted in a suitable manner from the top into a cylindrical container and positioned therein. Ultrasonic transducers are uniformly distributed over the whole cylindrical wall surface of this container. It can be assumed that the main radiation emission direction of each ultrasonic transducer is normal to the container wall into the container interior (see column 5, last par.). For the composition of a three-dimensional image of the breast being examined, an evaluation unit is described with a circuit so designed that various areas of the breast are first defined and then successively subjected to the ultrasound. To this end, for each impulse-echo procedure, only a single transducer or group of ultrasound transducers is energized for the emission of the ultrasound impulse and also for the reception of the returning sound echo by means of an electronic switch. The returning sound echo is filtered out by the determination of time windows.

DE 28 27 423 A1 discloses an apparatus for the determination of the internal structure of a body by means of sound radiation wherein a body is immersed in a container filled with a coupling medium and is subjected to ultrasound in this container. In this procedure, a sound beam is directed from one or several ultrasonic transducers through the body to at least one ultrasonic transducer serving as a receiver. The received signals are electronically processed in an evaluation unit, are stored and then the distribution of the sound refraction index and of the absorption coefficient are determined. In parallel therewith in the evaluation unit, using a point raster, a model of the body is composed which can be optimized by iterative sound measurements and which can be processed to individual cross-section images.

In a particular proposed embodiment, the sound transducers in the container are arranged in a matrix in the form of a cylinder. In that arrangement, a limited number of transducers must be activated as senders and also as receivers by an electronic switch wherein, for each active receiver, a subsequent amplifier, possibly with additional electronic stages (see page 24, paragraph 2), is provided. With this arrangement, transmission and scattering components and also echo components of the ultrasonic impulses can be received but they are not utilized for evaluation.

In a similar way, in the ultrasound apparatus disclosed in U.S. Pat. No. 5,673,697, a body is arranged in a container with ultrasonic transducers firmly mounted over the whole wall structure of the body and is exposed to ultrasound from at least one of those transducers with an ultrasound frequency of 1 to 5 MHz. All the other transducers can be employed successively by an electronic switch as receivers, whose signals are successively amplified for further processing and recorded. For the further processing the travel time, the phase and amplitude of the received ultrasound impulses are employed. By way of the reflection properties and sound speeds determined therefrom a three-dimensional image of the body is generated. The system however is not suitable for a reconstruction of rapid movements, since the time-delayed (non-simultaneous) recording of the receivers limits the time resolution to a large extent. Consequently, this publication does not provide any hint for a possible reconstruction of time-dependent changes in the body on a real-time basis.

It is the object of the present invention to provide a high-resolution ultrasonic tomograph, which provides for an improved resolution in the reconstruction of three-dimensional images in real time and with high image accuracy.

SUMMARY OF THE INVENTION

In a high resolution ultrasonic tomograph operating according to transmission, scattering and impulse-echo methods, comprising a container with an open top and including ultrasonic transducers arranged along the walls of the container, a coupling medium disposed in the container and a computer-based control and evaluation unit with a working memory, the control and evaluation unit is connected in a circuit with the ultrasonic transducers in such a way that the ultrasonic signal emitted from at least one ultrasonic transducer forms an ultrasonic impulse which is received by all the other transducers in parallel and is amplified, filtered and digitized to form electric signals which are stored in the working memory as a data set.

With such an ultrasound tomograph, for example in mammography, dynamic contrast medium examinations permit the reconstruction and evaluation of the female breast with very high time and spatial resolution.

The high-resolution ultrasound tomograph according to the invention will be described below in greater detail on the basis of the accompanying drawings.

DESCRIPTION OF A PREFERRED EMBODIMENT

Figure 1:
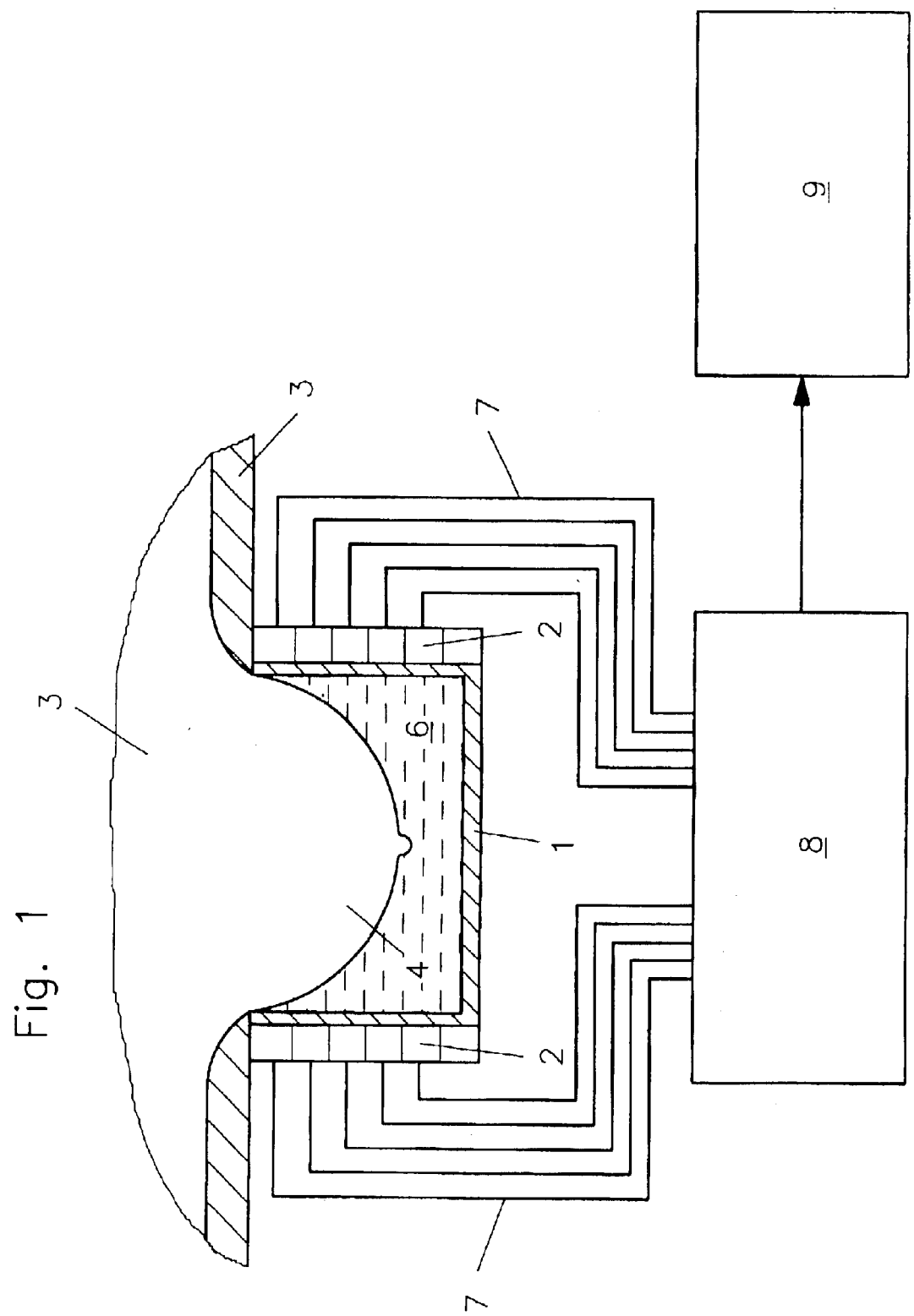
FIG. 1 shows the complete arrangement of the high-resolution ultrasonic tomograph for the ultrasound-supported mammography according to the invention.

FIG. 1 shows an exemplary arrangement of the high-resolution ultrasound tomograph for performing a mammography. It comprises a cylindrical container 1 with open top. Around the whole cylindrical wall surface ultrasonic transducers 2 are arranged. The open upper end of the container is fitted to an opening in a patient rest 3 into which a breast 4 of a patient 5 extends, who is laying on her stomach on the patient rest 3. For a low-loss transmission of ultrasound signals between the ultrasonic transducers 2 and the breast 4, a coupling medium 6 is disposed in the container 1, preferably a gel or a liquid, which wets the breast 4 to be examined and also the ultrasonic transducers 2.

Each of the ultrasonic transducers 2 present is independently connected by a suitably co-axial cable 7 to a computer-based control and evaluation unit 8, which also includes an operating data memory. The control and evaluation unit 8 is provided with a display device 9, preferably a monitor.

Figure 2:
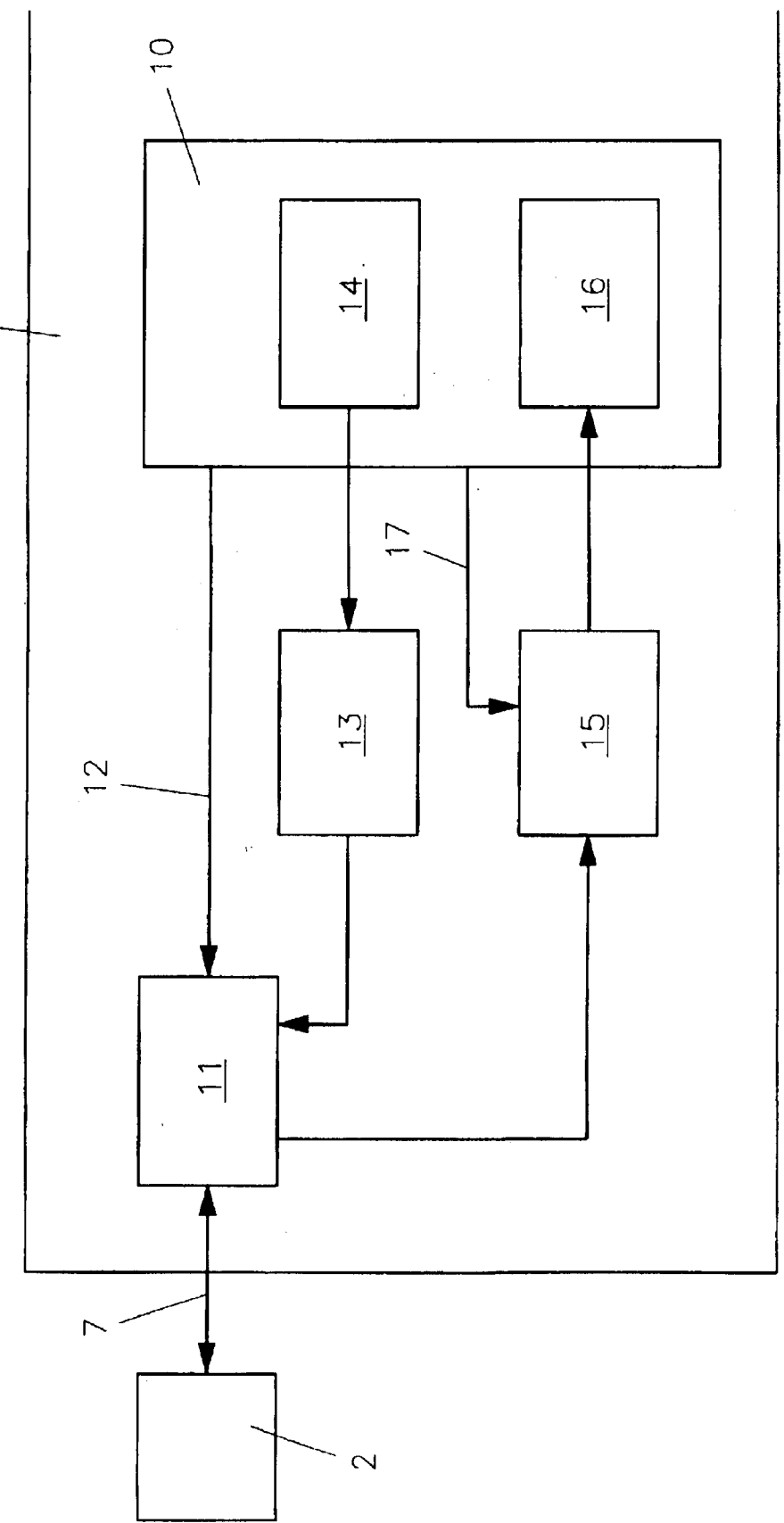
FIG. 2 shows schematically a circuit arrangement connecting any of the ultrasonic transducers of the high-resolution ultrasound tomograph with a computer of a control and evaluation unit.

FIG. 2 shows a circuit arrangement for the connection of any of the ultrasonic transducers 2 with the computer 10 of the control and evaluation unit 8. The ultrasonic transducer 2 is connected by way of a coaxial cable 7 to an electronic switch 11, by which the ultrasonic transducer 2 can be activated and switched for receiving or for sending sound signals. The electronic switch receives the respective switching signal by way of a control line 2 from the computer 10.

If the ultrasonic transducer 2 is activated as a signal transmitter, it receives from an impulse generator 13, which is triggered by a timer 14 in the computer 10, an electrical impulse which is transmitted by the transducer as a sound wave with the frequency of the ultrasonic transducer to the coupling medium.

If the ultrasonic transducer 2 is activated as a receiver, the signal received by the transducer 2 is supplied to an amplifier 15, in which the signal is amplified, filtered and digitized and the digital data signal is supplied to the operating memory 16 of the computer 10. In the operating memory 16, the data received from the transducer in its receiving state are stored on a time-dependent basis as data sets. The filtering of the signals in the amplifier eliminates background noise or static using frequency filters and provides for a selection of the signals for example by determining a time window. The filtering characteristics are transmitted as control signals from the computer 10 to the amplifier 15 by way of a control line 17.

With an ultrasound measurement during a mammography, an ultrasound impulse emitted from the ultrasonic transducers switched to a transmitter mode is received by all the transducers switched to the receiver mode and is processed into digital signals, which are stored as a data set in the operating memory. From the individual data of the data sets the computer reconstructs the three-dimensional image of the breast examined.

A local resolution can be optimized by a reduction of the time-based resolution quality. If, for example for a diagnosis, a momentary image with increased local resolution is required, it is possible to use for the reconstruction of the image different data sets from several immediately subsequent ultrasonic measurements employing in each case different ultrasonic transmitting transducers thereby viewing the object in each case from a different perspective. However, phenomena occurring rapidly in a breast being examined may result in the reconstruction in time-based error influences and must therefore be eliminated or corrected if necessary. But large time-dependent-errors are not to be expected with realistic repetition frequencies of the ultrasonic measurements. For example, with an assumed sound velocity in the coupling medium and in the breast of about 1500 m/s and a maximum travel distance of an ultrasound impulse in the container 1 of 0.50 m, a maximum repetition frequency of 2000 ultrasound measurements per second can be realized.

In another way, an improved local resolution can be achieved by selecting only a certain area in the breast to be examined wherein the signal is plotted only for a smaller time window so that it can be recorded with a correspondingly higher resolution. The conversion of the coordinates of the area of interest into corresponding control signals to the amplifier 15 occurs in the computer 10.

For the reconstruction of time-dependent processes, ultrasonic measurements should be repeated in periodically preselectable time spacings, wherein each data set represents the basis of an individual momentary image. Similar to a movie projection, the changes with time can be visualized as a series of reconstructed momentary images.

Specifically a breast or another body part to be examined is reconstructed as a three-dimensional image according to the following scheme:

It is first assumed that an ultrasonic impulse is radiated into the breast as a partially spherical wave, which is scattered in the breast at various points for example by refraction, deflection and reflection and which is measured at various receiver locations. Subsequently, assuming a constant sound speed in the measurement area, the sound velocity is determined considering only reflections of the first degree. Then all possible positions of the scattering points are disposed on an elliptic line around the transmitter and the receiver whose dimensions are determined by the measured sound travel time from the transmitter by way of any point on the ellipse to the receiver. For the accurate determination of a scattering point, the ellipses from equal-time measurements (equal ultrasound impulse) with different receivers are superimposed, wherein the points of intersection of the ellipses represent the scattering points and, for the reconstruction are assigned to a pixel with a gray or color scale.

If there are several scattering points, several ultrasound impulses are received by a receiving transducer and in each case, again an ultrasound impulse is generated. Otherwise, for the three-dimensional reconstruction of the breast examined, also the ellipses from as many as possible equal-time measurements are utilized and the scattering points determined are assigned to a pixel with a gray or color level. In order to eliminate noise or other static, it is appropriate to examine the phases of the ultrasound impulses received. If the signals are not summed up as absolute values, but as vectors, noise for example is averaged out of the result. Another possibility during the reconstruction is the transformation of a received signal into amplitude and phase by means of a Hibert transformation into a real and an imaginary component wherein the gray levels can be determined by a coherent addition of the individual signals.

The pixels are then assembled for every possible point in the container with the determined gray and color levels to form a reconstructed three-dimensional image.

The precision of the reconstruction is positively affected by the following influences:

The amplifiers as well as coupling medium 6 and the breast being examined can be described as linear systems.

there are only small speed variations.

The absorption capability of the breast can be calculated and corrected by the reflection reconstruction procedure.

Scattering centers are described as Huygen-type point sources.

Figure 3:
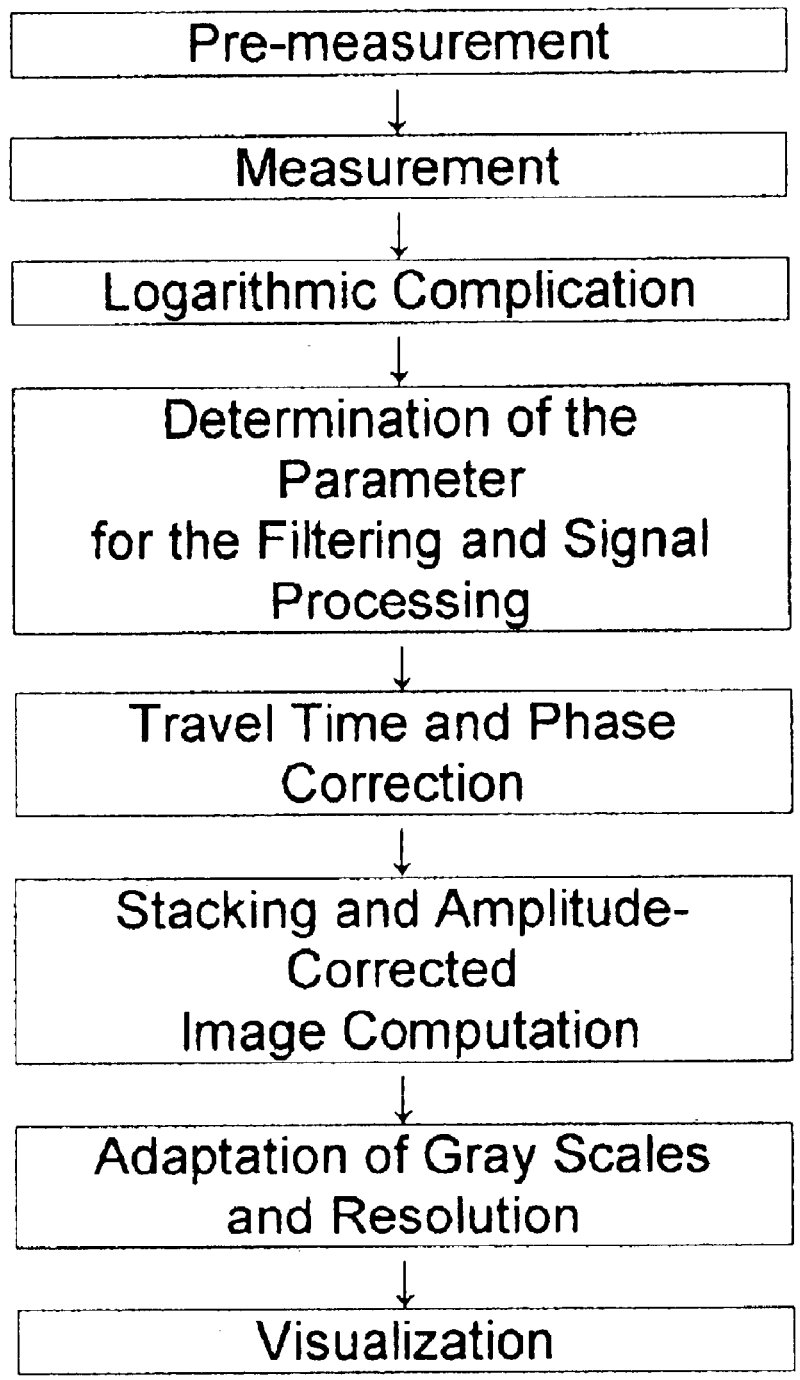
FIG. 3 is an overview of the various procedural steps for the reconstruction of a three-dimensional image.

In practice, the measuring and reconstruction procedure is performed by the steps described below (see FIG. 3). Pre-condition herefor is that the breast 4 to be examined is inserted into the container 1 and a sufficient amount of coupling medium for a complete wetting of the breast and the transducers is present in the container.

1. Pre-measurement

During the pre-measurement, the position of the breast 4 in the container 1 is determined with a few measurements utilizing the reflection capability of the skin in the coupling medium. In a first sub-step of the procedure, the temperature-dependent sound speed in the coupling medium is determined by way of a travel-time measurement with the known travel distance between the transmitting transducer and the receiving transducer and in a second sub-step the sound speed in the breast is determined.

2. Measurement

As described earlier, the measurement procedure is performed repeatedly with a predetermined repetition frequency. Herein, the ultrasonic transducers 2 installed in the container 1 are partially switched as transmitting transducers but all are used as receiver transducers. The ultrasound impulse should be provided in the container in the form of a partial sphere by a transmitting transducer or a correspondingly controlled group of transmitting transducers.

3. Logarithmic Amplification

During the measurements, the measuring signals are amplified analog-logarithmically for a compensation of amplitude differences of the received ultrasound impulses because of travel distance dependent attenuation. The analog logarithmic amplification makes it possible to limit the resolution during the digitizing (in the example, an 8-bit A/D converter is used) and consequently, the storage capacity to be provided for the measurement.

4. Determination of the Parameter for the Filtering and Signal Processing.

Based on the data of the pre-measurement, the computer 10 activates appropriate filter functions in the amplifier 15. This step contains particularly the determination of the resolution capability of the three-dimensional reconstruction by a selection of the pixel raster as well as the determination of a raster-based sound velocity table for the travel time correction during the reconstruction. For a reduction of the computing efforts required for the reconstruction a uniform sound speed may be employed for the coupling medium and for the breast. This step further includes a determination of the required scanning frequency. As pointed out earlier, the scanning frequency can be increased by a reduction of the resolution required for the reconstruction if a same-time data set is sufficient for the reconstruction of a momentary image.

5. Travel Time and Phase Correction

In this step, the travel time and phase errors in the coupling medium resulting from temperature changes are corrected. This is done by stretching or compressing the signals measured.

6. Stacking and Amplitude Corrected Image Computation

Stacking is the elimination of identical excess individual data. For example, the measured travel time of an ultrasound impulse is independent of the travel direction that is the transmission function between two transducers is independent of which of the two transducers is the transmitting transducer and which is the receiving transducer. With an amplitude correction, in support of the attenuation dependent coarse correction represented in step 3, a fine tuning with regard to the error influences present, preferably on the basis of the emission behavior of the active ultrasound transducers, is performed. Subsequently, the three-dimensional image is re-constructed with the aid of the algorithm described above by forming an ellipse for each individual measurement.

7. Adaptation of Gray Scales and Resolution

With this step, the resolution of the reconstructed image is reduced to the needed extent. In addition, following a reconstruction the color values can be changed for an improved reproduction.

What is claimed is:

1. A high-resolution ultrasonic tomograph according to the transmission, scattering and impulse echo method for the tissue examination of body extremities, particularly a female breast, said tomograph comprising: an open container including walls with ultrasonic transducers mounted on the walls so as to be directed toward the interior of the container which is filled with a coupling medium, by which the body part inserted into the container is wetted for the coupling and transmission of the ultrasonic wave signals between the ultrasonic transducers and the body part to be examined, and a computer-based control and evaluation unit with an operating memory connected in a circuit arrangement with the ultrasonic transducers in the container in such a way that:

a) any number of the ultrasonic transducers can be addressed for operation as transmitters and, respectively, as receivers by way of an electronic switch, b) the signals received by the addressed receivers are amplified as electrical signals, are filtered and digitized and stored as data in the operating memory, c) from the data in the operating memory, the sound travel times and from the sound travel times and the geometric conditions the individual travel speeds are determined and, by a division of the container volume in numerous areas and a suitable correlation between different data sets the sound velocities in the various areas are calculated, d) with the sound speeds in the various areas and the amplitude and the phases of the received signals, all the reflection points in the container are calculated, and e) the signals in the form of the data for the reflection points from all the measurements are added up for each point in the container, and for each point a color shade is assigned to each point corresponding to the level of the summed up value, and depending on the desired resolution this value is assigned to a pixel in the three-dimensional reconstruction, f) said ultrasonic signals emitted by the transmitting transducers forming an ultrasound impulse which is received by all receiving transducers in parallel and as an electrical signal amplified, filtered and digitized, is stored as a data set in the operating memory.

2. A high resolution ultrasonic tomograph according to claim 1, wherein said computer-based control and evaluation unit including the operating memory is connected with the ultrasound transducers in the open container in such a way that all ultrasound transducers are effective as receivers.

3. A high resolution ultrasonic tomograph according to claim 1, wherein said computer-based control and evaluation unit including the operating memory are connected in a circuit in such a way that the measuring procedure is repeated in short succession each time with another ultrasonic transducer or group of transducers, whereby, with each measuring procedure, a data set is generated and, with the utilization of several data sets for the generation of the three-dimensional reconstruction, the three-dimensional reconstruction has a time resolution which increases with increasing repetition frequency.

4. A high resolution ultrasonic tomograph according to claim 3, wherein the computer-based control and evaluation unit with an operating data memory is connected with the ultrasonic transducers in the open container in such a way that, with the determination of the color shades during the reconstruction, the amplitude and the phase of a signal are transformed by way of a Hibert transformation into a real and an imaginary signal component and the gray shades are determined by means of a coherent addition of the individual signals.

* * * * *